United States Patent [19]

Godfroid et al.

[11] Patent Number: 4,888,337
[45] Date of Patent: Dec. 19, 1989

[54] 5-OXY DERIVATIVES OF TETRAHYDROFURAN

[75] Inventors: Jean-Jacques Godfroid; Francoise Heymans, both of Paris; Pierre Braquet, Garches, all of France

[73] Assignee: Societe de Conseils de Recherches et d'Applications Scientifiques (S.C.R.A.S.), France

[21] Appl. No.: 144,238

[22] Filed: Jan. 15, 1988

[30] Foreign Application Priority Data

Jan. 27, 1987 [GB] United Kingdom ................ 8701727

[51] Int. Cl.$^4$ .................. A61K 31/395; A61K 31/34; C07D 405/12; C07D 307/12
[52] U.S. Cl. ..................................... 514/326; 514/336; 514/422; 514/471; 546/214; 546/283; 548/517
[58] Field of Search ................ 549/475; 546/214, 283; 548/517; 514/326, 336, 422, 471

[56] References Cited

U.S. PATENT DOCUMENTS 2,185,220  1/1940  Nabenhauer ........................ 549/492
4,289,884  9/1981  Barker ................................. 548/517
4,615,725  10/1986  Weissmuller et al. .............. 549/492

OTHER PUBLICATIONS

March, "Advanced Organic Chemistry", (Third Edition) (1985) (pp. 684–685) (McGraw Hill).

Primary Examiner—Robert T. Bond
Attorney, Agent, or Firm—Lucas & Just

[57]  ABSTRACT

This invention relates to:
(a) new tetrahydrofuran derivatives having the general formula I:

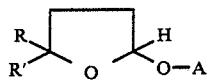

wherein either each of R and R' independently represents a hydrogen atom or various hydrocarbon substituents and A represents either a nitrogen containing ring or an alkylammonium salt or an alkylaminoacid rest;
(b) a process for the preparation of said compounds and
(c) therapeutic compositions containing said compounds as an active ingredient.

3 Claims, No Drawings

5-OXY DERIVATIVES OF TETRAHYDROFURAN

This invention relates to tetrahydrofuran derivatives having the general formula I:

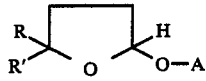
I wherein either each of R and R' independently represents a hydrogen atom, a straight chain or branched chain alkyl, alkenyl or alkynyl group having from 4 to 22 carbon atoms, a cycloalkyl or cycloalkenyl group having from 5 to 10 carbon atoms, a heterocyclic ring having 5 or 6 ring atoms of which one is a nitrogen, oxygen or sulphur atoms, or a group of the general formula:

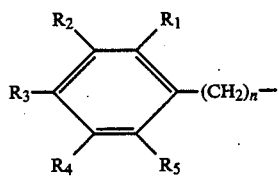

wherein n is zero or an integer of from 1 to 5 and either each of $R_1$, $R_2$, $R_3$, $R_4$ and $R_5$ independently represents a hydrogen, chlorine, bromine or iodine atom, a nitro, trifluoromethyl, trifluoromethoxy or trifluoromethylthio group or R and R' together form a cycloalkyl group having from 5 to 10 carbon atoms and wherein A represents:

a pyrrolidinium-alkyl or piperidinium-alkyl or pyridinium-alkyl salt of the formula

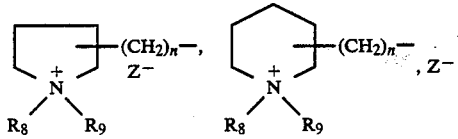

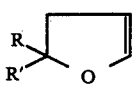

in which the alkyl group —$(CH_2)_n$— is of straight chain or branched chain configuration and has from 0 to 10 carbon atoms with each of $R_8$ and $R_9$ independently representing a hydrogen atom, a straight chain or branched chain alkyl or alkenyl group having up to 10 carbon atoms, a phenyl group or a phenylalkyl group, in which the alkyl group has from 1 to 5 carbon atoms,
an ammonium salt of formula:

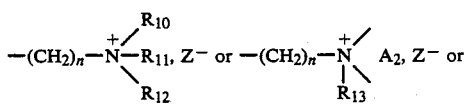

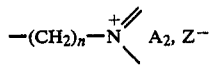

wherein $(CH_2)_n$ may be the substituted chain $$-CH_{2(m)}-\underset{\underset{OY}{|}}{CH}-(CH_2)_p-$$

wherein Y stands for alkyl or benzyle and m and p are such as both m and p$\geq$1 with m+p+1=n, said n being an integer of from 2 to 11, Z represents a pharmaceutically acceptable anion, each of $R_{10}$, $R_{11}$, $R_{12}$ and $R_{13}$ independently represents a $CH_3$ or $C_2H_5$ and the ring $NA_2$ is either an optionally substituted monocyclic ring containing 5 to 8 ring atoms of which one is nitrogen atom shown, another is a nitrogen or sulfur or oxygen atom, and the remainder are carbon atoms, or is such as —O—A is a dehydro residue of an aminoacide or of a short peptide, or an alkyl-$A_1$ group in which the alkyl group is of straight chain or branched chain configuration and has from 2 to 11 carbon atoms and $A_1$ represents an aminoacid linked to the chain through an ester or an amide function or a small peptide (2 or 3 aminoacids) or a glutathion.

The invention includes both the non separated mixtures of various possible diastereoisomers and enantiomers and also each separated diastereoisomer and enantiomer.

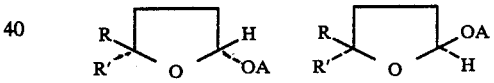

The invention relates also to a preparation process of compounds at formula I, said process comprising reacting a compound of formula II

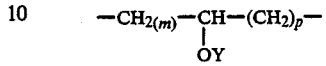
II wherein R and R' are as above defined with an excess of up to 10% of a compound of the general formula HOB wherein B is the precursor of A containing an amino group or a halo atom. The reaction is suitably carried out in an aprotic solvent (such as carbon tetrachloride, dimethylformamide or dimethylsulfoxide) at room temperature and in the presence of p-toluenesulphonic acid. Further conversion from B to A is achieved by treatment with an alkyl iodide when B contains an amino group or with a trialkylamine when B contains a halo atom.

The starting material of the general formula II may be prepared by pyrolysis of the corresponding acetate of the general formula III

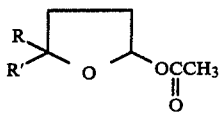

III at a temperature of 200° C. under reduced pressure.

The invention relates finally to therapeutic compositions of matter containing said compounds as an active ingredient therein.

EXAMPLE 1

2-(2-tridecyl-tetrahydrofuran-5-yloxy)-ethyl trimethylammonium iodide $R=CH_3(CH_2)_{12}$, $R'=H$, $A=(CH_2)_2N^+(CH_3)_3$, $I^-$ Step a: Preparation of 2-tridecyl-5-dimethylaminoethoxytetrahydrofuran:$A=(CH_2)_2N(CH_3)_2$ A solution of 0.2 g (2.2 mmol) of dimethylaminoethanol and 0.4 g (2.3 mmol) of dry p-toluenesulphonic acid in 50 ml of dry carbon tetrachloride was stirred at room temperature until all the amino-alcohol had been converted into its ammonium tosylate salt as determined by thin layer chromatography (chloroform:methanol 80:20 by volume). Then 0.5 g (2.mmol) of 2-tridecyl-2,3-dihydrofuran was added and the mixture was stirred in the same conditions until complete reaction of the dihydro compound as determined by TLC (petroleum ether:ether 90:10 by volume). After evacuation of the solvent under reduced pressure, the residue was diluted by 20 ml of a saturated aqueous sodium carbonate solution and extracted several times with diethyl ether. The diethyl ether phase was washed with water until neutrality, dried on anhydrous magnesium sulphate and filtered. The residue, after evaporation of water, was chromatographed on silica gel using successively mixtures of methanol:chloroform, from 1:99 to 20:80 by volume, to yield 0.5 g of the cis-trans title compound as an oil. NMR (80 MH$_z$, CDCl$_3$, HMDS*) $\delta$ 0.82 (t, 3H, CH$_3$ alkyl chain) 1.17 (large s, 22H, (CH$_2$)$_{11}$) 1.92 (m, 4H, CH$_2$—C—O) 2.17 (s, 6H, CH$_3$N) 2.42 (m, 4H, CH$_2$N+

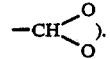

3.25–3.87 (m, 2H, CH$_2$O) 3.92 (m, 1H, CH—O) 4.95 (m, 1H,

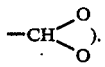

Step b: Preparation of 2-(2-tridecyl-tetrahydrofuran-5-yloxy)-ethyl trimethylammonium iodide 0.2 g (0.6 mmol) of the compound prepared in step (a) above and an excess of methyl iodide (0.85 g, 6 mmol) in 50 ml of dry acetone were stirred for two hours at room temperature. After evacuation of the solvent and of the excess of methyl iodide, the residue was chromatographed on a silica gel column using a mixture of methanol:chloroform (from 5% to 20% by volume of methanol) as eluent. After evaporation of the eluent, the title compound was obtained as a white solid melting at 93°–94° C. NMR (880 MH$_z$, CDCL$_3$, HMDS*) $\delta$ 0.80 (t, 3H, CH$_3$ alkyl chain) 1.20 (large s, 22H, (CH$_2$)$_{11}$) 1.35–2.05 (m, 6H, CH$_2$—C—O) 3.4 (s, 9H, CH$_3$N$^+$) 3.82 (m, 5H, CH$_2$N$^+$+CH$_2$—O+CH—O) 4.95 (m, 1H,

*HMDS means hexamethyl disiloxane and was used as standard.

EXAMPLE 2

2-(2-isobutyl-tetrahydrofuran-5-yloxy)-ethyl trimethylammonium iodide $R=(CH_3)_2CH-CH_2$, $R'=H$,
$A=(CH_2)_2N^+(CH_3)_3$, $I^-$ The title compound was obtained as described in Example 1 but starting with 2-isobutyl-2,3-dihydrofuran instead of 2-tridecyl-2,3-dihydrofuran. The product was a waxy solid. NMR (80 MH$_z$, CDCl$_3$, HMDS) $\delta$ 0.85 (d, 6H, CH$_3$) 1.12–2.15 (m, 7H, CH$_2$—C—O+CH) 3.37 (s, 9H, CH$_3$N$^+$) 3.6–4.15 (m, 5H, CH$_2$O+CH$_2$N$^+$+CH—O) 4.97 (m, 1H,

EXAMPLE 3

2-(2-heptyl-tetrahydrofuran-5-yloxy)-ethyl trimethylammonium iodide $R=CH_3(CH_2)_6$, $R'=H$, $A=(CH_2)_2N^+(CH_3)_3$, $I^-$ The title compound was obtained as described in Example 1 but starting with 2-heptyl-2,3-dihydrofuran instead of 2-tridecyl-2,3-dihydrofuran. The product was a low melting point compound. NMR (80 MH$_z$, CDCl$_3$, HMDS) $\delta$ 0.80 (t, 3H, CH$_3$ alkyl chain) 1.20 (large s, 10H, (CH$_2$)$_5$) 1.37–2.20 (m, 6H, CH$_2$—C—O) 3.37 (s, 9H, CH$_3$N$^+$) 3.6–4.25 (m, 5H, CH$_2$O+CH$_2$N$^+$+CH—O) 4.97 (m, 1H,

EXAMPLE 4

2-[2-(3,4,5-trimethoxyphenyl)-tetrahydrofuran-5-yloxy]ethyl trimethylammonium iodide

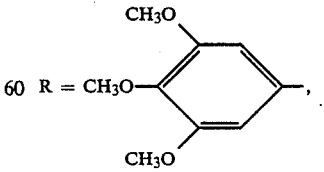

$R' = H$, $A = (CH_2)_2\overset{+}{N}(CH_3)_3$, $I^-$

The title compound was obtained as described in Example 1 but starting with 2-(3,4,5-trimethoxyphenyl)-

2,3-dihydrofuran instead of 2-tridecyl-2,3-dihydrofuran. The product was a highly hygroscopic compound. NMR (80 MHz, CDCl₃, HMDS) δ 2.00 (m, 4H, CH₂—C—O) 3.07-3,45 (m, 11H, CH₃N⁺+CH₂N⁺) 3.5–3.82 (m, 11H, CH₃—O+CH₂O) 4.85 (t, 1H,

)

5.15 (m, 1H,

)

6.35 (m, 2H, ArH).
(Ar means aromatic ring).

EXAMPLE 5

2-(cyclohexanespiro-2-tetrahydrofuran-5-yloxy)-ethyl trimethylammonium iodide

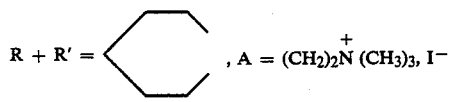

The title compound was obtained as described in Example 1 but starting with 2,3-dihydro-cyclohexanespiro-2-furan instead of 2-tridecyl-2,3-dihydrofuran. The product was a wax. NMR (80 MHz, CDCl₃, HMDS) δ 5.12 (m, 1H,

), 3.87 (m, 4H, OCH₂+CH₂N⁺), 3.52 (s, 9H, CH₃N⁺), 2.25–1.12 (m, 14H, CH₂).

EXAMPLE 6

3-(2-tridecyl-tetrahydrofuran-5-yloxy)-propyl trimethylammonium iodide

The title compound was obtained as described in Example 1 but starting with 3-dimethylamino-propanol instead of dimethylamino-ethanol. The product was a pale yellow solid melting at 81° C., NMR (80 MHz, CDCl₃, HMDS) δ 0.80 (t, 3H, CH₃ alkyl chain) 1.20 (large s, 11H, (CH₂)₁₁) 1.35–2.20 (m, 8H, CH₂—C—O) 3.37 (s, 9H, CH₃N⁺) 3.12–4.05 (m, 5H, CH₂O+CH₂N⁺+CH—O) 4.92 (m, 1H,

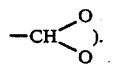

EXAMPLE 7

4-[2-(3,4,5-trimethoxyphenyl)-tetrahydrofuran-5-yloxy]N-methyl N-ethyl-piperidinium iodide

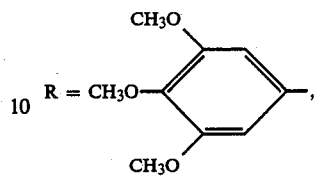

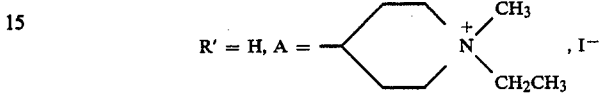

The title compound was obtained as described in Example 1 but starting with 4-hydroxy-N-ethyl-piperidine instead of dimethylamino-ethanol. The product was a brown wax. NMR (80 MHz, CDLCl₃, HMDS) δ 6.57 (m, 2H, ArH), 5.32 (m, 1H,

), 4.97 (m, 1H,

), 3.82 (large s, 9H, CH₃O), 3.92–3.12 (m, 10H, CH—O+CH₂N⁺+CH₃N⁺), 2.35–1.61 (m, 8H, CH₂), 1.33 (t, 3H, CH₃).

EXAMPLE 8

2-(2-tridecyl-tetrahydrofuran-5-yloxy)-ethyl trimethylammonium bromide, cis and trans

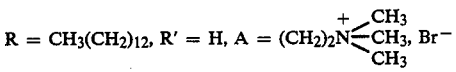

Step a: Preparation of 2-tridecyl-5-(2-bromoethoxy)-tetrahydrofuran cis and trans: A=(CH₂)₂Br To 2 g (8 mmol) of 2-tridecyl-2,3-dihydrofuran an 1.1 g (8.8 mmol) of 2-bromo-ethanol in 50 ml of carbon tetrachloride were added 20 mg (0.1 mmol) of dry p-toluene-sulphonic acid. After stirring overnight at room temperature, the solvent was evacuated under reduced pressure. The residue was diluted with a aqueous solution of sodium carbonate and extracted with diethyl ether. The organic phase was washed with water and then dryed on anhydrous magnesium sulphate. The solvent was removed by evaporation and the residue was chromatographed on silica gel using 10% by volume diethyl ether in petroleum ether as eluent. This method allowed the recovery, as oils, of first the trans title compound (896 mg) then a mixture of both cis and trans isomers (419 mg) and, finally, the cis isomer (340 mg) as confirmed by their spectral data: NMR (250 MHz, CDCl₃, TMS*) δ

5.16 (dd,1H,R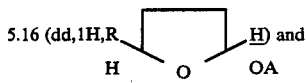) and 4.05 (quintet,1H,R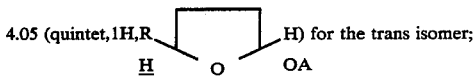) for the trans isomer;

δ 5.09 (d, 1H, R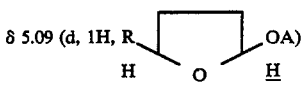)

and 4.01 (quintet, 1H, R) for the cis isomer.

*TMS = tetramethyl silane used as standard.

Step b: Preparation of trans-2-(2-tridecyl-tetrahydrofuran-5-yloxy)-ethyl trimethylammonium bromide 0.2 g (0.5 mmol) of the trans isomer prepared in step (a) above and 10 ml of a mixture of chloroform:isopropanol:dimethylformamide (3:5:5, by volume) were cooled in an ice bath and saturated with about ten times (0.3 g, 5 mmol) the theoretical amount of gaseous trimethylamine. The mixture was then stirred for two hours and gradually heated to 60°–70° C. Evaporation of the solvents and of the excess of trimethylamine gave a white solid in the remaining dimethylformamide; the solid was treated with petroleum ether and, after filtration, gave the title compound as a white powder melting at 148° C.

NMR (80 MHz, CDCl3, HMDS) δ 4.95 (m, 1H,

4.12–3.62 (m, 5H, CH—O+CH2O+CH2N+), 3.40 (s, 9H, (CH3)3N+), 2.32–1.5 (m, 6H, CH2—C—O), 1.2 (large s, 22H, (CH2)11), 0.8 (t, 3H, CH3).

Step c: Preparation of cis 2-(2-tridecyl-tetrahydrofuran-5-yloxy)-ethyl trimethylammonium bromide This compound was obtained as described in step (b) above but starting with the cis isomer prepared in step (a) above. The product was a white powder melting at 154° C.

NMR (80 MHz, CDCl3, HMDS) δ 4.90 (m, 1H,

other signals are the same as for the trans isomer.

EXAMPLE 9

6-[2-hexadecyl-tetrahydrofuran-5-yloxy]-hexyl pyridinium chloride cis and trans

R = C16H33, R' = H, A = (CH2)6N+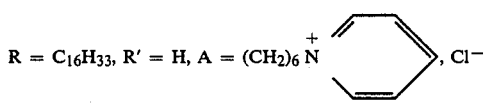, Cl−

Analogous to Example 8 but (step a) using dimethylformamide as solvent starting from 2-hexadecyl-2,3-dihydrofuran and 6-chlorohexanol instead of 2-bromoethanol to give the trans and the cis 2-hexadecyl-5-(6'-chloro)-hexyloxy-tetrahydrofuran and (step b) performing the substitution of the chloro atom by pyridine by heating (60°–80° C.) 0.3 g (0.7 mmol) of each chloro compound, pyridine (2 ml) and dimethylformamide (2 ml) overnight with stirring. Evaporation of the excess of pyridine and dimethylformamide leaded to residus which were chromatographed on silica gel using successively 10, 15 and 20% MeOH in CHCl3 as eluents. The title compounds were recovered as waxy solids.

trans isomer: NMR (80 MHz, CDCl3, HMDS) δ 9.76 (d, 2H,

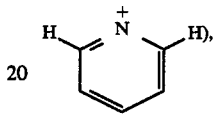), 8.63 (m, 1H, 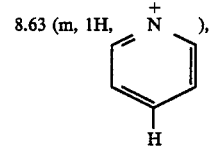), 8.31 (t, 2H, 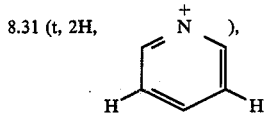), 5.16 (m, 1H,

), 4.27–3.20 (m, 5H, CH—O+CH2O+CH2N+), 2.4–1.52 (m, 10H, CH2—C—O+CH2—C—N+), 1.25 (large s, 32H, (CH2)14+(CH2)2 in the center of the hexyl moiety, 0.83 (t, 3H, CH3).

cis isomer: NMR analogous to the trans isomer except for

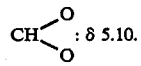 : δ 5.10.

EXAMPLE 10

6-[2-hexyl-tetrahydrofuran-5-yloxy]-hexyl-thiazolium-chloride

R = C6H13, R' = H, A = (CH2)6N+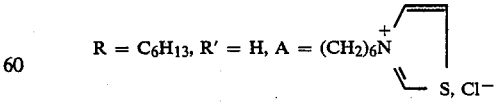

Analogous to example 9 but starting from 2-hexyl-2,3-dihydrofuran and 6-chlorohexanol. Substitution of the chloro atom was performed with thiazole instead of pyridine in the same conditions but on a mixture of cis+trans isomers leading to the title compound as an highly hygroscopic compound.

NMR (80 MH$_z$, CDCl$_3$, HMDS) δ 10.53, 8.60, 8.33 (3H, thiazolium), 5.05 (m, 1H,

4.0 (m, 1H, CH—O), 3.6 (t, 2H, CH$_2$O), 3.4 (t, 2H, CH$_2$N$^+$), 2.27–1.52 (m, 10H, CH$_2$—C—O+CH$_2$—C—N$^+$), 1.3 (large s, 12H (CH$_2$)$_4$+(CH$_2$)$_2$ of the (CH$_2$)$_6$ moiety), 0.81 (t, 3H, CH$_3$).

EXAMPLE 11

3-[2-cyclopentyl-tetrahydrofuran-5-yloxy]-propyl-pyridinium bromide

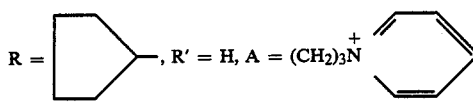

Analogous to example 9(a)(b) but starting from 2-cyclopentyl-2,3-dihydrofuran and 3-bromopropanol to yield the title compound as a viscous oil. NMR (80 MH$_z$, CDCl$_3$, HMDS) δ 9.58, 8.65, 8.23 (5H, pyridinium), 5.08 (m, 1H,

4.17–3.35 (m, 5H, CH—O+CH$_2$O+CH$_2$N$^+$), 2.32 (m, 2H, O—CH$_2$—C—N$^+$), 2.20–1.55 (m, 7H, CH$_2$—C—O+CH of the cyclopentyl moiety), 1.25 (m, 8H, CH$_2$ of the cyclopentyl moiety).

EXAMPLE 12

6-(2-p-trifluoromethyl-benzyl-tetrahydrofuran-5-yloxy)-hexyl quinolinium chloride

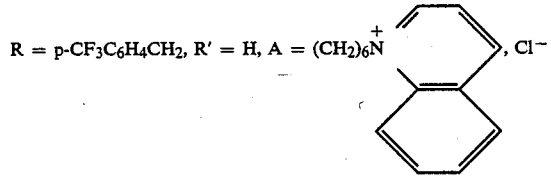

Analogous to example 9 starting from 2-p-trifluoromethylbenzyl-2,3-dihydrofuran in step (a) and using quinolein instead of pyridine in step (b) to yield the title compound as a viscous product. NMR (80 MH$_z$, CDCl$_3$, HMDS) δ 10.75 (1H), 9.06 (1H), 8.25 (5H) (m, quinolinium), 8.58 (m, 4H, C$_6$H$_4$), 5.1 (m, 1H,

4.2–3.1 (m, 7H, CH—O, CH$_2$O, CH$_2$N and CF$_3$φCH$_2$) 2.38–1.5 (m, 10H, CH$_2$—C—N$^+$ and CH$_2$—C—O), 1.25 (m, 4H, (CH$_2$)$_2$ of the hexyl moiety).

EXAMPLE 13

2-(2-o-chlorophenyl-ethyl-tetrahydrofuran-5-yloxy)-ethyltrimethylammonium iodide

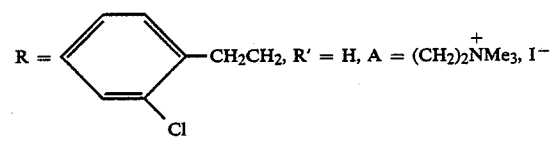

Analogous to example 1(a)(b) starting from 2-φ-chlorophenylethyl-2,3-dihydrofuran, to obtain the title compound as a waxy solid. NMR (80 MH$_z$, CDCl$_3$, HMDS) δ 7.12 (m, 4H, C$_6$H$_4$), 5.0 (m, 1H,

3.5–4.1 (m, 5H, CH$_2$O+CH$_2$N+30 CH—O), 3.32 (s, 9H, CH$_3$N$^+$), 2.75 (t, 2H, ClφCH$_2$), 2.20–1.10 (m, 6H, CH$_2$—CO).

EXAMPLE 14

3-(2-eicosyl-tetrahydrofuran-5-yloxy)-methyl N-methylpyridinium iodide

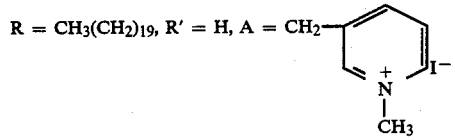

Step a: Preparation of 2-eicosyl-5-(pyridino-3')-methoxy tetrahydrofuran:

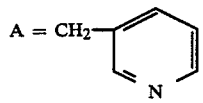

A solution of 0.3 g (2.8 mmol) of pyridine-3 methanol and 0.5 g (3 mmol) of dry p-toluene sulphonic acid in 20 ml of dry dimethylsulfoxide was stirred at room temperature until all the amino alcohol had been converted into its ammonium tosylate salt, as determined by thin layer chromatography (chloroform/methanol 80:20 by volume). Then 1 g (2.8 mmol) of 2-eicosyl-2,3-dihydrofuran was added and the mixture was stirred in the same conditions until complete reaction of the dihydro compound as determined by TLC (petroleum ether/ether, 90:10 by volume). After evacuation of the solvent under reduced pressure, the residue was treated as described in Example 1 step (a) to yield 0.8 g of the cis-trans title compound as an oil.

NMR (80 MH$_z$, CDCl$_3$, HMDS) δ 8.67 (m, 2H, 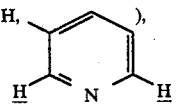

7.76 (d, 1H, ), 7.35 (m, 1H, 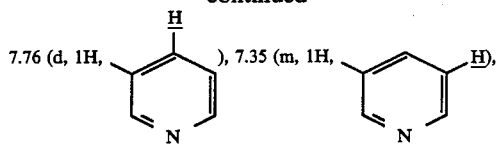), 5.25 (m, 1H, CH⟨O/O⟩), 4.82, 4.47 (2d, syst AB, 2H, CH₂—O), 4.1 (m, 1H, CH—O), 2.25-1.5 (m, 6H, CH₂—C—O), 1.25 (large s, 36H, (CH₂)₁₈, 0.85 (t, 3H, CH₃).

Step b: Preparation of 3-(2-eicosyl tetrahydrofuran-5-yloxy)-methyl N-methyl pyridinium iodide:

The title compound was obtained as described in Example 1 step (b), startng from the compound prepared in step (a). Waxy solid. NMR (80 MHz, CDCl₃, HMDS) δ

9.25 (m, 2H, H—C=N⁺), 8.5 (d, 1H, ),

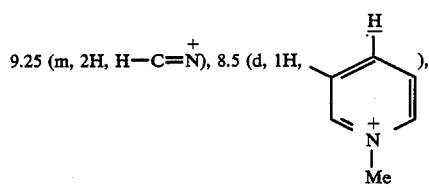

8.17 (t, 1H, H), 5.26 (m, 1H, CH⟨O/O⟩), 4.85 (d, 2H, OCH₂), 4.72 (s, 3H, CH₃N⁺), 4.08 (m, 1H, CHO), 2.22-1.33 (m, 6H, CH₂—C—O), 1.25 (large s, 36H, (CH₂)₁₈), 0.85 (t, 3H, CH₃).

EXAMPLE 15

3-[(2-hexyl-tetrahydrofuran-5-yloxy) 2-ethoxy]-propyl N-methyl piperidinium iodide

R = CH₃—(CH₂)₅,

R' = H, A = CH₂—CH—CH₂N⁺⟨piperidinyl⟩
         |
         CH₃CH₂O           CH₃

Step a: Preparation of 3-[(2-hexyl-tetrahydrofuran-5-yloxy)-2-ethoxy]-propyl piperidine.

A = CH₂—CH—CH₂N⟨piperidinyl⟩
        |
        OEt

Analogous to Example 14 step (a) starting from 2-hexyl-2,3-dihydrofuran and (3-hydroxy 2-ethoxy)-propyl piperidine to give the cis-trans title compound as an oil.

NMR (80 MHz, CDCl₃, HMDS) δ 5.05 (m, 1H,

CH⟨O/O⟩), 3.35 (m, 2H, CH—O), 3.82-3.25 (m, 4H, CH₂O), 2.40 (m, 6H, CH₂N), 2.15-1.36 (m, 10H, CH₂—C—O+CH₂—C—N), 1.21 (large s, 10H, (CH₂)₄+CH₂ piperidinyl), 1.12 (t, 3H, CH₃—C—O), 0.82 (t, 3H, CH₃).

Step b: Preparation of 3-[(2-hexyl-tetrahydrofuran-5-yloxy)-2-ethoxy]-propyl N-methyl piperidinium iodide.

Analogous to Example 1 step (b) starting from the compound prepared above in step (a). The title compound was recovered as a low melting point solid.

NMR (80 MHz, CDCl₃, HMDS) δ 5.05 (m, 1H,

CH⟨O/O⟩), 4.0 (m, 2H, CH—O), 3.91-3.27 (m, 10H, CH₂—O+CH₂N⁺), 3.41 (s, 3H, CH₃N⁺), 1.86 (m, 10H, CH₂—C—O+CH₂—C—N⁺), 1.25 (large s, 10H, (CH₂)₄+CH₂ piperidinyl), 1.13 (t, 3H, CH₃—C—O), 0.82 (t, 3H, CH₃).

EXAMPLE 16

3-[(2-hexadecyl-tetrahydrofuran-5-yloxy)-2-amino]propionic acid methyl ester

R = CH₃(CH₂)₁₅, R' = H, A = CH₂CHCO₂CH₃
                                    |
                                    NH₂

Analogous to Example 1 but starting with 2-hexadecyl-2,3-dihydrofuran and serine methyl ester to yield the title compound as a hygroscopic product.

IR (film) 3380 (NH₂), 2920, 2860 (CH), 1745 (C=O), 1030 (C—O—C).

NMR (80 MHz, CDCl₃, HMDS) δ 5.12 (m, 1H,

CH⟨O/O⟩), 4.25-3.62 (m, 4H, CH—O, CH₂O+

CHO),
‖
O 3.8 (s, 3H, CO₂CH₃), 3.27 (m, exchangeable with D₂O, 2H, NH₂), 2.25-1.55 (m, 6H, CH₂—C—O), 1.27 (large s, 28H, (CH₂)₁₄, 0.85 (t, 3H, CH₃).

EXAMPLE 17

6-(2-hexyl-tetrahydrofuran-5-yloxy)-hexyl 4'-phenyl pyridinium chloride cis and trans

R = C₆H₁₃, R' =

H, A = (CH₂)₆N⁺ 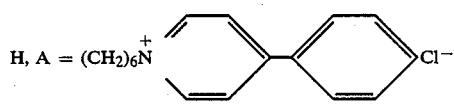 Cl⁻

Analogous to Example 8(a) starting from 2-hexyl 2,3-dihydrofuran and 6-chlorohexanol instead of 2-bromoethanol to give the trans and the cis 2-hexyl 5-(6'- chloro)-hexyloxy tetrahydrofuran (b) substitution of the chloro atom by 4-phenyl pyridine was performed by heating (60°-80° C). 0.45 g (1.5 mmoles) of each chloro compound, dimethylformamide (2 ml) and 1 g (7.5 mmoles) of 4-phenyl pyridine overnight with stirring. Evaporation of dimethylformamide leaded to residues which were chromatographed on silica gel using 10% MeOH in CHCl$_3$ as eluent. The title compounds were recovered as waxy solids.

trans isomer: NMR (80 MH$_z$, CDCl$_3$, HMDS) δ

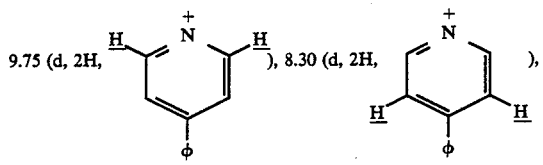

9.75 (d, 2H, ...), 8.30 (d, 2H, ...), 7.40 (m, 5H, C$_6$H$_5$), 5.15 (m, 1H,

), 4.25–3.20 (m, 5H, CHO+CH$_2$O+CH$_2$N+), 2.38–1.50 (m, 10H, CH$_2$—C—O+CH$_2$—C—N+), 1.23 (large s, 12H, (CH$_2$)$_4$+(CH$_2$)$_2$ in the center of the hexyl moiety between O and N), 0.82 (t, 3H, CH$_3$).

cis isomer: NMR analogous to the trans isomer except for

δ: 5.10 ppm.

TOXICOLOGY

The compound of the invention has been administrated to mice for determination of acute LD$_{50}$. For all the compounds of the invention LD$_{50}$ was over 600 mg/kg.

PHARMACOLOGY

A proof of the pharmaceutical interest of the compounds of the invention has been established by the following pharmaceutical experimentations:

(1)—Inhibition of the platelets aggregation on New Zealand rabbits

The experimentation was conducted on platelets with plasma of New Zealand rabbits. Blood samples were taken from auricular artery and placed in a citrate buffer (3.8%; pH 7.4); blood was further centrifugated for 15 mn at 1 200 RPM. The tested sample was prepared in DMSO, then poured on platelets rich plasma for 1 mn, then a dose of 2.5 nM of PAF was added. The determination is made on a Cronolog Coultronics apparatus which determines the transmission percentage corresponding to the maximum height of the peak before the desaggregation. The percentage of variation of the inhibition with respect to the transmission percentage is calcutated (control: pure DMSO). This method was described in details in LABORATORY INVESTIGATIONS, Vol. 41, No. 3, p. 275, 1979, JEAN-PIERRE CAZENAVE, Dr. MED., JACQUES BENVENISTE, DR. MED., and J. FRASER MUSTARD, M.D., "Aggregation of Rabbits Platelets by Platelet-Activating Factor Is Independent of the Release Reaction and the Arachidonate Pathway and Inhibited by Membrane-Active Drugs".

(2)—Action in Platelet-Activating Factor (PAF) involvement in endotoxin-induced thrombocitopenie in rabbits In this test the controls consisted in a rabbit batch (6) administered intravenously with 1 μg/kg of PAF: this adminstration resulted in a reference thrombocitopenie. For determining the action of all the compounds of the invention, further batches of each 6 rabbits were treated each with a 10 mg/kg i.p. dose of the selected product of the invention then 10 mn later, with intravenous injection of PAF as above indicated; PAF is considered as a mediator of endotoxin shock. In order to determine whether the compounds of the invention contribute to the prevention of thrombocitopenie or leukopenie in endotoxin shock, E. Coli endotoxin (0.03 mg/kg) ws intravenously injected in rabbits. Pretreatment with the compounds of the inventions (10 mg/kg i.p) significantly reduced the thrombocitopenie at 60 mn (from 21 to 64%) and 180 mn (from 16 to 68%) after the endotoxin injection.

(3)—Asthma

The myotropic activities of PAF-acether, leukotriene B$_4$, leukotriene D$_4$ and histamine were compared on superfused guinea-pig parenchymal strip and were shown to have the following order of potency: PAF-acether>LTD$_4$>LTB$_4$>histamine. The contractile response of the lung parenchyma to PAF-acether was inhibited by aspirin and imidazole which suggested that thromboxane A$_2$ might play a mediator role in PAF-induced contractions. Neither an antagonist of leukotriene D$_4$ nor an antihistamine, mepyramine, had any effect of PAF contractions. The activity of all the compounds of the invention as antogonists of PAF was also studied on superfused lung parenchyma contracted by histamine, leukotriene B$_4$, leukotriene D$_4$ and PAF-acether.

These compounds were without effect on the histamine response but they slightly reduced the contractions elicited by leukotriene D$_4$ and potentiated those by leukotriene B$_4$. The compounds of the invention (7.1×10$^{-6}$M) inhibited by 23–76%, average value 63% the contraction induced by 5.7×10$^{-13}$M PAF-acether and by 26–71%, average value 52% that inducted by 5.7×10$^{-10}$M PAF-acether.

POSOLOGY

In human administration as, generally used doses are from 100 to 400 mg per diem.

We claim:

1. Tetrahydrofuran derivatives having the formula I:

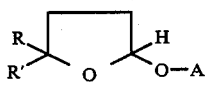

wherein either each of R and R' independently represents a hydrogen atom, a straight chain or branched chain alkyl, alkenyl or alkynyl group having from 4 to 22 carbon atoms, a cycloalkyl or cycloalkenyl group having from 5 to 10 carbon atoms, or a group of the formula:

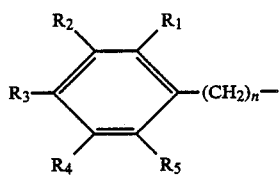

wherein n is zero or an integer of from 1 to 5 and either each of $R_1$, $R_2$, $R_3$, $R_4$ and $R_5$ independently represents a hydrogen, chlorine, bromine or iodine atom, a nitro, methoxy, trifluoromethyl, trifluoromethyoxy or trifluoromethylthio group or R and R' together form a cycloalkyl group having from 5 to 10 carbon atoms and wherein A represents:
  a pyrrolidinium-alkyl or piperidinium-alkyl or pyridinium-alkyl salt of the formula

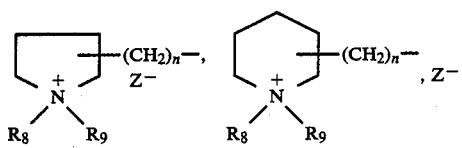

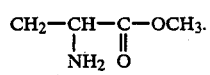

in which the alkyl group $-(CH_2)_n-$ is of straight chain or branched chain configuration and has from 0 to 10 carbon atoms with each of $R_8$ and $R_9$ independently representing a hydrogen atom, a straight chain or branched chain alkyl or alkenyl group having up to 10 carbon atoms, a phenyl group or a phenylalkyl group, in which the alkyl group has from 1 to 5 carbon atoms, or
  an ammonium salt of formula:

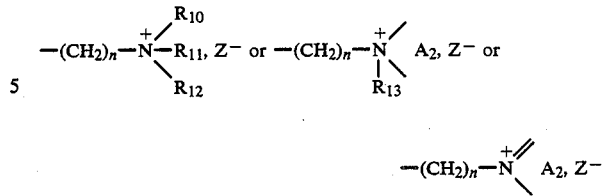

wherein $(CH_2)_n$ may be the substituted chain

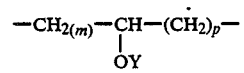

wherein Y stands for ethyl or benzyle and m and p are such as both m and $p \geq 1$ with $m+p+1=n$, said n being an integer of from 3 to 11, Z represents a pharmaceutically acceptable anion, each of $R_{10}$, $R_{11}$, $R_{12}$ and $R_{13}$ independently represents a $CH_3$ or $C_2H_5$ and the ring $NA_2$ is either an unsubstituted or phenyl substituted monocyclic ring containing 5 to 8 ring atoms of which one is the nitrogen atom shown, one of the other atoms of the ring being selected from the group consisting of nitrogen, sulfur or carbon and, when said one other atom is not carbon, said atom being non-adjacent to said nitrogen atom shown; or a pyridinium ring; or $$CH_2-CH-C-OCH_3.$$
$$\phantom{CH_2-C}|\phantom{-C}\|$$
$$\phantom{CH_2-C}NH_2\ O$$

2. Isolated isomers or non separated mixtures of various possible diastereoisomers and enantiomers of compounds of claim 1.

3. A therapeutic composition of matter comprising as an active ingredient therein a sufficient amount of a compound according to claim 2 to be effective in the treatment of asthma associated with an appropriate diluent or carrier.

* * * * *

UNITED STATES PATENT AND TRADEMARK OFFICE
CERTIFICATE OF CORRECTION

PATENT NO. : 4,888,337

DATED : December 19, 1989

INVENTOR(S) : Jean-Jacques Godfroid et al.

It is certified that error appears in the above-identified patent and that said Letters Patent is hereby corrected as shown below:

Column 7, lines 1-19; replace the formulas therein with the following formulas:

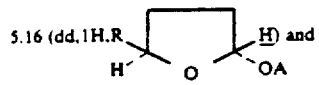

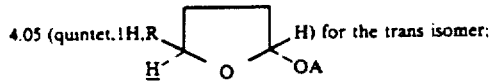

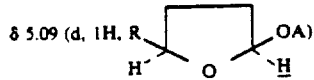

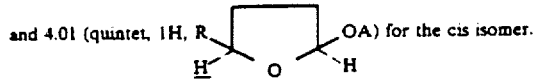

*TMS = tetramethyl silane used as standard.

Column 9, line 66, change "$CH_2N$" to --$CH_2\overset{+}{N}$--.

UNITED STATES PATENT AND TRADEMARK OFFICE
CERTIFICATE OF CORRECTION

PATENT NO. : 4,888,337  Page 2 of 2

DATED : December 19, 1989

INVENTOR(S) : Jean-jacques Godfroid, et al.

It is certified that error appears in the above-identified patent and that said Letters Patent is hereby corrected as shown below:

Column 10, line 23, delete "30" and insert a "+" sign over the "N".

Signed and Sealed this

Twentieth Day of November, 1990

Attest:

HARRY F. MANBECK, JR.

Attesting Officer    Commissioner of Patents and Trademarks